US007811821B2

(12) United States Patent
Slukvin et al.

(10) Patent No.: US 7,811,821 B2
(45) Date of Patent: Oct. 12, 2010

(54) METHOD OF FORMING DENDRITIC CELLS FROM EMBRYONIC STEM CELLS

(75) Inventors: Igor I. Slukvin, Verona, WI (US); James A. Thomson, Madison, WI (US); Maksym A. Vodyanyk, Madison, WI (US); Maryna E. Gumenyuk, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 282 days.

(21) Appl. No.: 11/443,608

(22) Filed: May 31, 2006

(65) Prior Publication Data

US 2006/0275901 A1 Dec. 7, 2006

Related U.S. Application Data

(60) Provisional application No. 60/686,145, filed on Jun. 1, 2005.

(51) Int. Cl.
C12N 5/00 (2006.01)
C12N 5/02 (2006.01)
C12N 5/071 (2010.01)

(52) U.S. Cl. ............... 435/377; 435/373; 435/366; 435/372; 435/385

(58) Field of Classification Search ............... 435/373, 435/377
See application file for complete search history.

(56) References Cited

U.S. PATENT DOCUMENTS

| 6,280,718 | B1 | 8/2001 | Kaufman et al. |
| 7,615,374 | B2 | 11/2009 | Slukvin et al. |
| 2002/0019047 | A1 | 2/2002 | Waldmann et al. |
| 2002/0131962 | A1 | 9/2002 | Waldmann et al. |
| 2006/0063255 | A1 | 3/2006 | Lebkowski et al. |
| 2007/0072295 | A1 | 3/2007 | Slukvin et al. |
| 2008/0003674 | A1 | 1/2008 | Slukvin et al. |
| 2008/0233610 | A1 | 9/2008 | Slukvin et al. |
| 2009/0081784 | A1 | 3/2009 | Slukvin et al. |

FOREIGN PATENT DOCUMENTS

| JP | 2003-108677 | 4/2003 |
| SE | 531979 C2 | 9/2009 |
| WO | WO 01/36589 A2 | 5/2001 |
| WO | WO 01/51616 A2 | 7/2001 |
| WO | 2006/022330 A | 3/2006 |
| WO | WO 2006/022330 A | 3/2006 |

OTHER PUBLICATIONS

Thomson, J. Science, 1998, 282:1145-1147.*
Habibian, 1998, J.Exp. Med. 188:393-398.*
Gong, J., et al., "Fusions of Human Ovarian Carcinoma Cells with Autologous or Allogeneic Dendritic Cells Induce Antitumor Immunity," J. Immun., 165:1705-1711(2000).
Odorico, J.S., et al., "Multilineage Differentiation from Human Embryonic Stem Cell Lines," Stem cells 19:193-204 (2001).
Parkhurst, M.R., et al., "Hybrids of Dendritic Cells and Tumor Cells Generated by Electrofusion Simultaneously Present . . . ," J. Immunology 170:5317-5325 (2003).
Shamblott, M.J., et al., "Human Embryonic Germ Cell Derivatives Express a Broad Range of Developmentally Distinct . . . ," Proc. Natl. Acad. Sci. U.S.A. 98:113-118 (2001).
Zhan, X., et al., "Functional antigen-presenting leucocytes derived from human embryonic stem cells in vitro," Lancet 364:163-171 (2004).
Vodyanik, Maxim A et al. "Human embryonic stem cell . . . " Blood vol. 105 No. 2: 617-626 (2005).
Senju S et al. "Generation and genetic modification . . . " Blood, W.B. Saunders Company, Orlando, FL vol. 101 No. 9 3501-3508 (2003).
Slukvin Igor I et al. "Development of lymphohematopoietic . . . " Blood, W.B. Saunders Company, Orlando, FL vol. 104, No. 11 p. 763A (2004).
Szabolcs P et al. "Expansion of immunostimulatory denritic cells . . . " Journal of Immunology vol. 154, No. 112, pp. 5851-5861 (1995).
Kyung Ha Ryu et al. "In vitro generation of functional . . . " International Journal of Hematology vol. 80, No. 3, pp. 281-286 (2004).
Martinez Del Hoyo Gloria et al. "Characterization of a common precursor . . . " Nature (London) vol. 415, No. 6875, pp. 1043-1047 (2002).
Slukvin Igor I et al. "Directed differentiation of human embryonic stem cells . . . " Journal of Immunology vol. 176, No. 5, pp. 2924-2932 (2006).
Scott-Taylor, T.H.; Human tumour and dendritic cell hybrids generated by electrofusion: potential for cancer vaccines; Biochemica et Biophysica Acta; 2000; p. 265-279; Elsevier Science B.V.
Ginis I, et al., "Differences between human and mouse embryonic stem cells," Dev. Biol. 269:360-380 (2004).
Xu R, et al., "Basic FGF and suppression of BMP signaling sustain undifferentiated proliferation of human ESCs," Nat. Methods 2:185-190 (2005).
Odorico J, et al., "Multilineage differentiation from human embryonic stem cell lines," Stem Cells 19: 193-204 (2001).
Daheron L, et al., "LIFISTAT3 signaling fails to maintain self-renewal of human embryonic stem cells," Stem Cells 22:770-778 (2004).
Xu R, et al., "BMP4 initiates human embryonic stem cell differentiation to trophoblast," Nat. Biotechnol. 20: 1261-1264 (2002).
Li F, et al., "Bone morphogenetic protein 4 induces efficient hematopoietic differentiation of rhesus monkey embryonic stem cells in vitro", Blood 98:335-342 (2001).
Li F, et al., "Hematopoietic differentiation in vitro of rhesus monkey embryonic stem cells," Blood 92:368a (1998).

(Continued)

Primary Examiner—Valarie Bertoglio
(74) Attorney, Agent, or Firm—Quarles & Brady LLP

(57) ABSTRACT

This invention relates to the culture of dendritic cells from human embryonic stem (ES) cells. Human ES cells are first cultured into hematopoietic cells by co-culture with stromal cells. The cells now differentiated into the hematopoietic lineage are then cultured with GM-CSF to create a culture of myeloid precursor cells. Culture of the myeloid precursor cells with the cytokines GM-CSF and IL-4 causes functional dendritic cells to be generated. The dendritic cells have a unique phenotype, as indicated by their combination of cell surface markers.

4 Claims, 4 Drawing Sheets

OTHER PUBLICATIONS

Geijtenbeek TB, et al., "Marginal zone macrophages express a murine homologue of DC-SIGN that captures blood-borne antigens in vivo", Blood 100(8):2908-2916 (2002).

Hamann J, et al., "EMR1, the human homolog of F4/80, is an eosinophil-specific receptor", Eur J Immunol., 37 (10):2797-2802 (2007).

Forsyth N, et al., "Telomerase and differentiation in multicellular organisms: turn it off, turn it on, and turn it off again," Differentiation 69:188-197 (2002).

Swedish Patent Application No. 0702695-8 Office action dated Oct. 8, 2008.

Swedish Patent Application No. 0702695-8 response to the Oct. 8, 2008 Office action.

European Patent Application No. 06771688.6 Office action dated Feb. 19, 2009.

European Patent Application No. 06771688.6 response to the Feb. 19, 2009 Office action.

Great Britain Patent Application No. 0723152.5 Office action dated Sep. 22, 2009.

Singapore Patent Application No. 200718257-9 Office action dated Jan. 19, 2010.

Great Britain Patent Application No. 0816154.9 Office action dated Oct. 1, 2008.

Great Britain Patent Application No. 0816154.9 response to the Oct. 1, 2008 Office action.

Great Britain Patent Application No. 0816154.9 Office action dated Oct. 30, 2009.

U.S. Appl. No. 11/672,724 Office action dated May 15, 2009.

U.S. Appl. No. 11/672,724 response to the May 15, 2009 Office action.

U.S. Appl. No. 11/672,724 Office action dated Dec. 17, 2009.

U.S. Appl. No. 11/520,871 Office action dated Nov. 3, 2009.

U.S. Appl. No. 11/520,871 response to the Nov. 3, 2009 Office action.

U.S. Appl. No. 12/024,770 Office action dated Dec. 15, 2008.

U.S. Appl. No. 12/024,770 response to the Dec. 15, 2008 Office action.

Great Britain Patent Application No. 0723152.5 response to the Sep. 22, 2009 Office action.

* cited by examiner

METHOD OF FORMING DENDRITIC CELLS FROM EMBRYONIC STEM CELLS

CROSS-REFERENCE TO RELATED APPLICATIONS

This application claims the benefit of U.S. provisional application 60/686,145, filed Jun. 1, 2005, incorporated by reference within.

STATEMENT REGARDING FEDERALLY SPONSORED RESEARCH OR DEVELOPMENT

This invention was made with United States government support awarded by the following agency:
DOD ARPA DAMD 17-02-C-0130
The United States has certain rights in this invention.

BACKGROUND OF THE INVENTION

Embryonic stem cells are pluripotent cells capable of both proliferation in cell culture as well as differentiation towards a variety of lineage restricted cell populations that exhibit multipotent properties (Odorico et al., (2001) *Stem Cells* 19:193-204). Human embryonic stem (ES) cells are thus capable of commitment and differentiation to a variety of lineage-restricted paths resulting in very specific cell types that perform unique functions.

Generally, ES cells are highly homogeneous, exhibit the capacity for self-renewal, and have the ability to differentiate into any functional cell in the body. This self-renewal property can lead under appropriate conditions to a long-term proliferating capability with the potential for unlimited expansion in cell culture. Furthermore, it is understood, that if human ES cells are allowed to differentiate in an undirected fashion, a heterogeneous population of cells is obtained expressing markers for a plurality of different tissue types (WO 01/51616; Shamblott et al., (2001) *Proc. Natl. Acad. Sci. U.S.A.* 98:113). These features make these cells a unique homogeneous starting population for the production of cells having therapeutic utility.

There have been efforts by researchers in the field to develop methods to culture a variety of progeny cell types from human ES cells. For example, U.S. Pat. No. 6,280,718 describes a method for culturing human ES cells into hematopoietic cells by culturing the human ES cell with stromal cells. Some methods of creating progeny cell types from human ES cells involve the creation of embryoid bodies, which are three dimensional structures which can be formed by ES cells in culture and which foster the diverse differentiation of ES cells into various differentiated progeny lineages. Other methods for creating progeny lineages depend on the culturing of human ES cells with particular media, agents or types of cells to expose the ES cells to factors which encourage differentiation in a particular direction. All these methods have a common objective, which is to provide a source for particular cell types for scientific research and experimentation and, for some cell types, for ultimate transplantation into human bodies for therapeutic purposes.

Dendritic cells are immune cells that perform a critical function in the mammalian immune system. Dendritic cells (sometimes here DCs) are powerful antigen-presenting cells which are present at low frequency in tissues of the body in contact with the environment such as skin, and linings of the nose, lungs, stomach and intestines. Dendritic cells have the ability to uptake antigens and induce primary T cell responses to initiate generalized immune system responses to pathogens. Dendritic cells are so named because of their long processes or arms, called dendrites, that are characteristic of dendritic cell morphology.

Dendritic cells are generated continuously in the bone marrow from the hematopoietic lineage and mature in the blood. The dendritic cells of an individual have heterogeneous phenotype and function. Dendritic cells develop in several ways, and there may be differences among the dendritic cells depending on their lineage of derivation. Dendritic cells that develop from CD34+ hematopoietic progenitors along two independent pathways become Langerhans cells and interstitial dendritic cells. Dendritic cells derived from monocytes or from plasmocytoid T cells are referred to as monocyte-derived DCs or plasmocytoid DCs respectively. On the basis of their cellular origin phenotype, dendritic cells are normally classified broadly into two major divisions, myeloid or lymphoid. It was believed that myeloid DCs were developed from a common myeloid precursor while lymphoid DCs developed from a common lymphoid precursors, although it has now also been proposed that a common myeloid DC precursor gives rise to all dendritic cell lineages.

The availability of human immature dendritic cells would be useful for the study of antigen processing and presentation, as well as for understanding the mechanisms of the induction of immunity and tolerance. Functional analysis of human dendritic cell subsets was significantly facilitated by the development of in vitro systems for the differentiation of dendritic cells from CD34+ hematopoietic stem cells and monocytes. However, using these existing protocols, obtaining large numbers of human dendritic cell progenitors is a laborious process and is associated with potential risks for donors. Other aspects of dendritic cell biology, such as dendritic cell ontogeny, have not been studied in humans due to the difficulties in obtaining tissues during early development. The advent of human ES cells represents an opportunity to overcome these limitations.

Functional dendritic cells have been generated from mouse ES cells using embryoid bodies and by co-culture with mouse macrophage colony-stimulating factor deficient bone-marrow stromal cell line, OP9. We have previously demonstrated that OP9 cells can be used to induce hematopoietic cells from human ES cells. The full potency of those hematopoietic cells to produce progeny of the various lineages was unexplored previously.

BRIEF SUMMARY OF THE INVENTION

In one embodiment, the present invention is a method of culturing human embryonic stem cells into dendritic cells, the method comprising the steps of co-culturing human embryonic stem cells with stromal cells that do not express macrophage colony-stimulating factor, wherein the stem cells are induced to differentiate into multipotent lympho-hematopoietic progenitor cells and wherein the culture is not in the presence of cytokines; culturing the progenitor cells with granulocyte/macrophage colony stimulating factor (GM-CSF) to cause the expansion of myeloid precursors cells; and recovering cells which have the phenotype of immature dendritic cells. Preferably the step of recovering cells with the phenotype of dendritic cells includes culturing the myeloid precursor cells with at least one cytokine selected from the group consisting of IL-4, TNF-α, IFN-α, and GM-CSF. Preferably, the stromal cells are OP9 cells and the culturing of step (b) is under non-adherent conditions. In another embodiment, the present invention includes the step of culturing the myeloid precursor cells with GM-CSF and TNFα or GM-CSF and IFN-α and recovering regulatory accessory cells, wherein the regulatory accessory cells are characterized by the markers CD1a$^{low}$, CD9-, CD80$^{low}$ and CD86$^{low}$.

The present invention is also a culture of human dendritic cells, in which a majority of the cells in the culture have a phenotype of CD1a+, DC-SIGN+, CD4+, CD9$^{low}$, CD11c+, CD40$^{low}$, CD86+, CD80+, CD86+, HLA-ABC+, HLA-DR+, and are negative for CD207 and CD208. Preferably, at least 70% of the cells in the culture have the phenotype.

In another embodiment, the invention is a culture of myeloid precursor cells in which a majority of the cells have a phenotype of myeloid precursors and in which an excess of 90% of the cells are CD45+, CD4+, CD123$^{low}$, negative for HLA-DR and include subpopulations of cells expressing MPO, M-CSFR, CD11b, CD11c, CD15 and CD16.

In another embodiment, the present invention is a method of making of cellular vaccine, comprising differentiating human embryonic stem cells into population of dendritic cells, characterized by the markers CD1a, CD80, CD86, DC-SIGN, HLA-DR$^{high}$, obtaining and preparing single cell suspension of tumor cells from a patient, and fusing the embryonic stem cell-derived dendritic cells with the tumor cells so that a cellular vaccine is created. Other embodiments of the present invention will be apparent to one of skill in the art after review of the specification, claims and drawings.

BRIEF DESCRIPTION OF THE SEVERAL VIEWS OF THE DRAWINGS

FIG. 2A is a phase-contrast micrograph of differentiated human ES cells growing in the presence of GM-CSF. FIG. 2B is a Wright-stained cytospin of cells obtained from that culture. FIG. 2C charts the colony forming cell (CFC) potential of the expanded cells (counts are mean of five experiments). FIG. 2D are graphs of data from representative experiments demonstrating expression of surface and intracellular myeloid markers on GM-CSF expanded human ES cells.

DETAILED DESCRIPTION OF THE INVENTION

We report here that dendritic cells can be created in large numbers from human ES cells. The co-culture system with a macrophage colony-stimulating factor (M-CSF) deficient stromal cell line, such as the murine line OP9, fosters the differentiation of human ES cells into hematopoietic cells. These hematopoietic cells have the capacity to generate dendritic cells, a capacity which is exploited by GM-CSF culture of the hematopoietic cells. The dendritic cells derived from human ES cells are morphologically, phenotypically and functionally comparable to interstitial human dendritic cells naturally produced in vivo.

Slukvin, et al., *J. Immunology,* 2006, 176:2924-2932, is an academic article by the inventors describing the present invention. It is incorporated by reference as if fully set forth below.

Figure 1A:
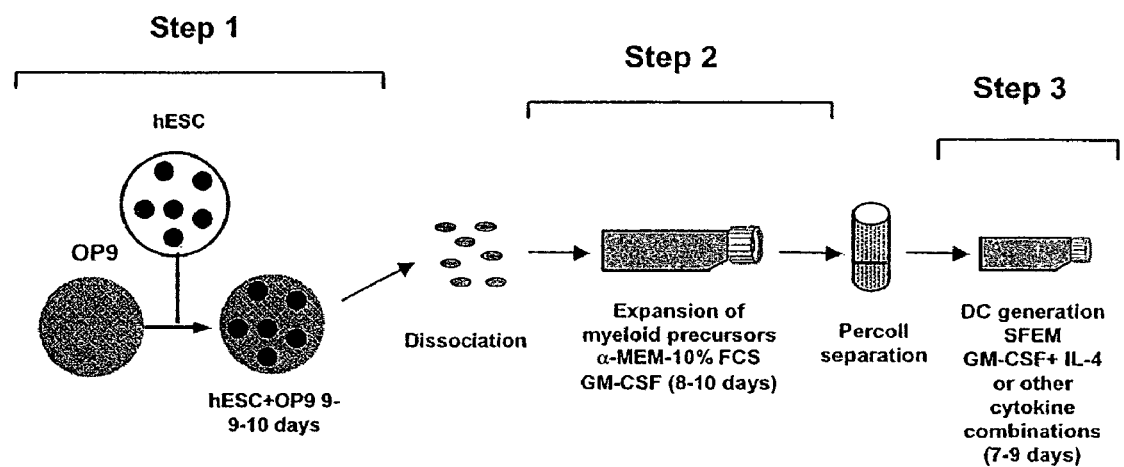
FIGS. 1A and B are schematic illustrations of the overall method of the present invention.
Figure 1B:
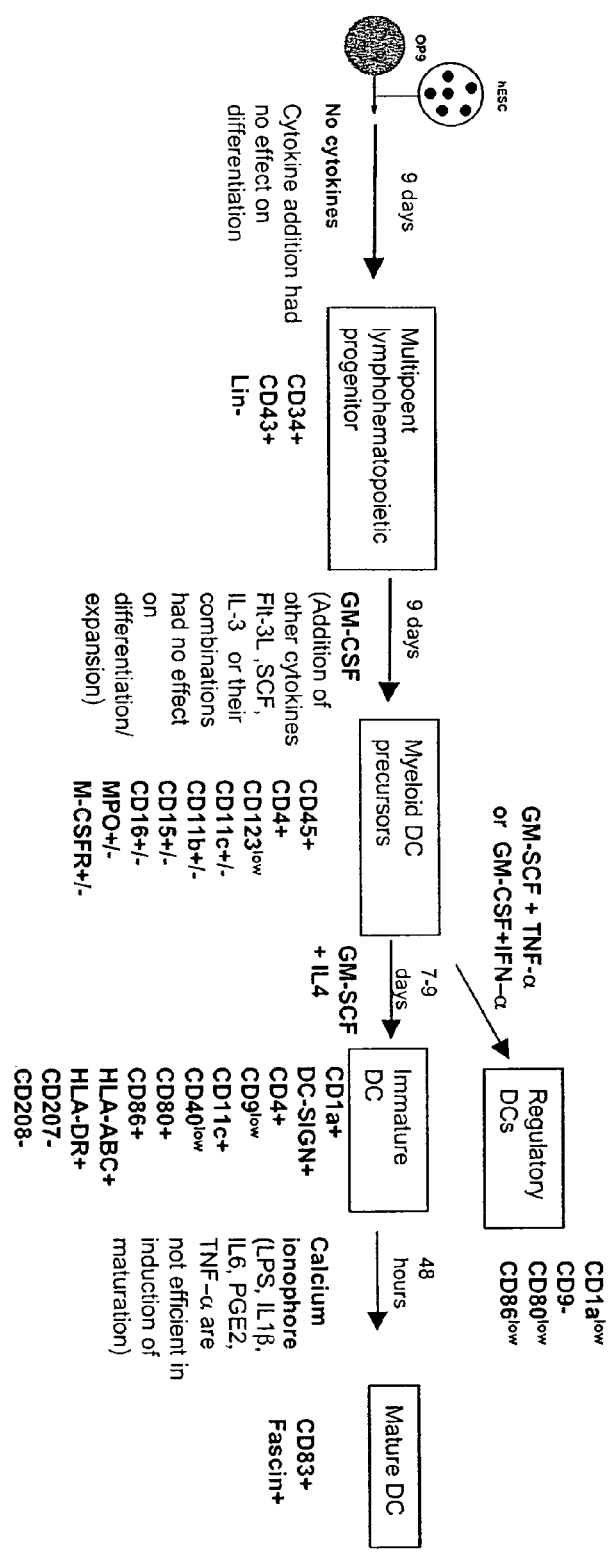

The overall method is schematically illustrated in FIGS. 1A and B, in which the process is broken down into three overall steps and is demonstrated in its preferable form in the Examples below and in Slukvin, 2006, supra. By "multipotent lymphohematopoietic progenitor cells," "myeloid dendritic cell (DC) precursor cells," "immature DC," "mature DC," and "regulatory DC," we mean the cell populations disclosed in FIG. 1B.

In Step 1, human ES cells are co-cultured with stromal cells, preferably M-CSF deficient stromal cells, to induce differentiation of the cells into multipotent lymphohematopoietic progenitor cells. Preferably, the cells are OP9 cells.

In Step 2, the disassociated ES-derived cells from that culture are then cultured so that myeloid cell expansion occurs. Preferably, this is done by culture of the cells with granulocyte/macrophage colony stimulating factor (GM-CSF) preferably as described below in the Examples. Also preferably, this step is performed in non-adherent conditions. Preferable non-adherent conditions require the tissue culture flask to be coated with poly 2-hydroxyethyl methacrylate (HEMA, Sigma) as described below. One could also prevent cell adherence by other means, such as cell shaking, using substances known to have non-adherent properties to cover the plastic container or using commercially available non-adherent tissue flasks.

The result of this expansion step is a culture rich in myeloid precursors, and that culture is then used in Step 3 to make dendritic cells by culture in serum free medium with GM-CSF and IL-4, or other combination of cytokines (as described below) which condition development to dendritic cells.

An optional separation procedure, which can be done with Percoll separation, is shown between steps 2 and 3 and is used to remove both clumps of cells and dead cells from the culture prior to inducing dendritic cell formation.

In the examples described below, dendritic cells are generated from human ES cells by selective expansion of myeloid precursors obtained by the co-culture of human ES cells with M-CSF-deficient stromal cells without cytokine addition. The hematopoietic cells resulting from the co-culture step are competent to be induced to differentiate into myeloid precursor cells and then into immature dendritic cells.

A critical step in our protocol for generating DCs was the efficiency of hematopoietic differentiation in human ES cell/OP9 co-culture. Co-cultures with a low number of CD34+CD43+Lin− multipotent lymphohematopoietic progenitors (less than 3%) failed to expand myeloid precursors and, subsequently, differentiate to dendritic cells. "Lin−" indicates that these progenitors do not express CD11b, CD14, CD2, CD3, CD7, CD19, CD38, CD45RA, and HLA-DR markers present on more mature cells committed to specific hemotopoietic lineage.

We used the entire cell suspension from the co-culture, rather than isolated lymphohematopoietic precursors for the next step in which granulocyte/macrophage colony stimulating factor (GM-CSF) is used to mediate expansion of myeloid precursors which are capable of differentiating into dendritic cells. In our hands, the most effective factor to cause the myeloid precursor cells to undergo this expansion was GM-CSF, in contrast to other factors, such as SCF and FLT3-L, which in our hands had little effect on the expansion of myeloid dendritic cell precursors.

The myeloid precursors derived from human ES cells and expanded with GM-CSF, contained myeloid colony-forming cells (CFCs), as well as small populations of more mature cells with the dendritic cell phenotype. However, the majority of the cells morphologically resembled blasts of the myelomonocytic lineage and expressed CD4, CD45, CD123$^{low}$ and low levels of CD14. These cells were HLA-DR-negative. We found that these cells included subpopulations of cells expressing MPO, M-CSFR, CD11b, CD11c, CD15, and CD16.

The human ES cell-derived immature dendritic cells obtained by our method had a phenotype of CD1a+, DC-SIGN+, CD4+, CD9$^{low}$, CD11c+, CD40$^{low}$, CD80+, CD86+, HLA-ABC+, HLA-DR+, CD207– and CD208–, a phenotype comparable with interstitial dendritic cells differentiated from the cord blood or bone marrow CD34+ hematopoietic stem cells. Preferably, at these immature dendritic cells comprise at least 70% of the cultured cells at this point. However, a distinct phenotypic feature of the human ES-derived dendritic cells was co-expression of CD14. The level of CD14 expression was the lowest in cells differentiated using IL-4, but was substantially higher on cells differentiated using TNF-α. Dendritic cells that develop from human CD34+ hematopoietic stem cells in the presence of GM-CSF and TNF-α differentiate into Langerhans cells and dermal and interstitial dendritic cells through intermediates that have phenotypes that are CD1a+CD14– and CD1a–CD14+ respectively. So far, in our cultures, CD1a expression has always been associated with at least low level expression of CD14, and we have not seen distinct CD1a+CD14– or CD1a–CD14+populations in our cell cultures. Thus the culture conditions used for differentiation of the human ES cells into dendritic cells appears to use unique pathways that may not exact replicates of the corresponding pathways of differentiation from CD45+ hematopoietic stem cells in vivo.

The Examples below describe another embodiment of the present invention, a population of cells, wherein at least 70% are mature DCs.

Additionally, another embodiment of the invention is a population of regulatory DC cells. Myeloid DC precursors cultured with GM-CSF and TNF-α or GM-CSF and IFN α develop into CD1a$^{low}$, CD9–, CD80$^{low}$, CD86$^{low}$ accessory cells with low stimulatory activity. These cells can represent regulatory DCs.

The co-culture system used here with the M-CSF deficient stromal cells (OP9 cells) differs from the system based on OP9 cells used with murine ES cells. The method described here does not use a second co-culture with the OP9 cells, unlike the mouse system. We collected the human ES cell derivatives from the co-culture when the maximal amount of myeloid progenitors were generated and then expanded those progenitors with GM-CSF in feeder-free non-adherent conditions. This technique resulted in the discrete population of dendritic cell precursors which is useful for further studies of dendritic cell development.

It has been shown recently that during embryoid body differentiation, cells expressing HLA-DR and capable of triggering proliferation of adult lymphocytes were generated. Zhan, et al., 2004,. *Lancet* July 10; 364(9429):163-71. However, the antigen-presenting properties and the phenotype of the cells generated in this system were not demonstrated. It is possible that cells obtained as described in this report were macrophages. Our results provide, for the first time, evidence that human ES cells can be directly differentiated into cells with morphology, phenotype and functional properties of antigen-presenting dendritic cells. Furthermore, this process is already relatively efficient. We have been able to grow as many as $4\times10^7$ dendritic cells at a time from $10^7$ initially plated human ES cells.

While dendritic cells have evident scientific interest and application, they also have potential use in human medicine. Several studies have demonstrated that peptide-pulsed dendritic cells transferred in vivo were able to induce efficiently anti-tumor immune response in mice. These studies have encouraged subsequent development of dendritic cell-based vaccines for cancer immunotherapy in humans. In these techniques, immature dendritic cell precursors isolated from peripheral blood or dendritic cells generated from peripheral blood mononuclear cells and CD34+ hematopoietic progenitors are used in clinical trials of dendritic cell based vaccines. However, these techniques are laborious, require repeated generation of new dendritic cells for each vaccination and are difficult to standardize. Embryonic stem cells can be expanded without limit and can differentiate into multiple types of cells, and therefore can be universal and scalable source of cells for dendritic cell vaccines. Potentially, dendritic cells with major HLA haplotype combinations can be obtained from human ES cells to match donor MHC haplotype. In the clinical setting, human ES cell-derived dendritic cells would have several advantages over dendritic cells from conventional sources. Large absolute numbers of dendritic cells could be generated from the same donor cell line, and the same line of dendritic cells could be used for multiple vaccinations. Derivation of dendritic cells from human ES cells can be less laborious and more amendable for standardization with implementation of bioreactor technology. Low risk of pathogen contamination and risk free donor collection are another important advantages of clinical use of human ES cell-derived dendritic cells.

In another embodiment, the present invention is a method of making a cellular vaccine, comprising differentiating the human embryonic stem cells into a population of dendritic cells, characterized in that they are CD1a$^+$, CD80$^+$, CD86$^+$, DC-SIGN$^+$, HLA-DR$^{high}$, obtaining and preparing single cell suspension of tumor cells from a patient, and fusing the embryonic stem cell-derived dendritic cells with cancer cells. Gong, et al., *J. Immunology,* 2000, 165:1705-1711 and Parkhurst, et al., 2003, *J. Immunology,* 170:5317-5325 (both incorporated by reference) describe general techniques for cellular fusion.

In another embodiment, the invention is a method of forming a dendritic cell vaccine for treating of cancer, comprising dendritic cells differentiating from human embryonic stem cells, where dendritic cells have been fused with allogeneic cancer cells. One of skill in the art would understand and appreciate the various methods of creating tumor vaccines. For example, U.S. Patent Application Publications US2002/0131962 A1 and US2006/0063255 A1 disclose several methods.

In another embodiment, the present invention is a method of making a dendritic cell vaccine for treating cancer, comprising differentiating human embryonic stem cells into CD45+CD4+CD123$^{low}$ low myeloid precursors which include subpopulations of cells expressing CD11b, CD11c, and CD16, genetically altering the myeloid precursors to express immunogenic tumor proteins/peptides, and differentiating the genetically modified myeloid precursors into immunogenic dendritic cells. For example, one may wish to transfect cells with tumor genes that will be the target of an immune response. For example, one may wish to transfect cells with melanoma-antigen-3 (MAGE-3), prostatic acid phosphatase (PAP) or prostate specific membrane antigen (PSMA).

In another embodiment, the present invention is a method of making dendritic cells with tolerogenic properties which can be used for treatment of rejection of human embryonic stem cell-derived tissues obtained from the same cell line. By "tolerogenic properties," we mean that the cell suppresses rejection of a transplant by the host immune system. The cells will down-regulate a detrimental immune response of the host towards a transplanted tissue. For this purpose hES cell-derived myeloid precursors will be induced to differentiate into regulatory DCs by culture with GM-CSF and TNF-α or GM-CSF and IFN α.

EXAMPLES

Experimental Protocol and Results

Expansion of Human ES Cell-Derived Myeloid Progenitors with GM-CSF.

Figure 2:
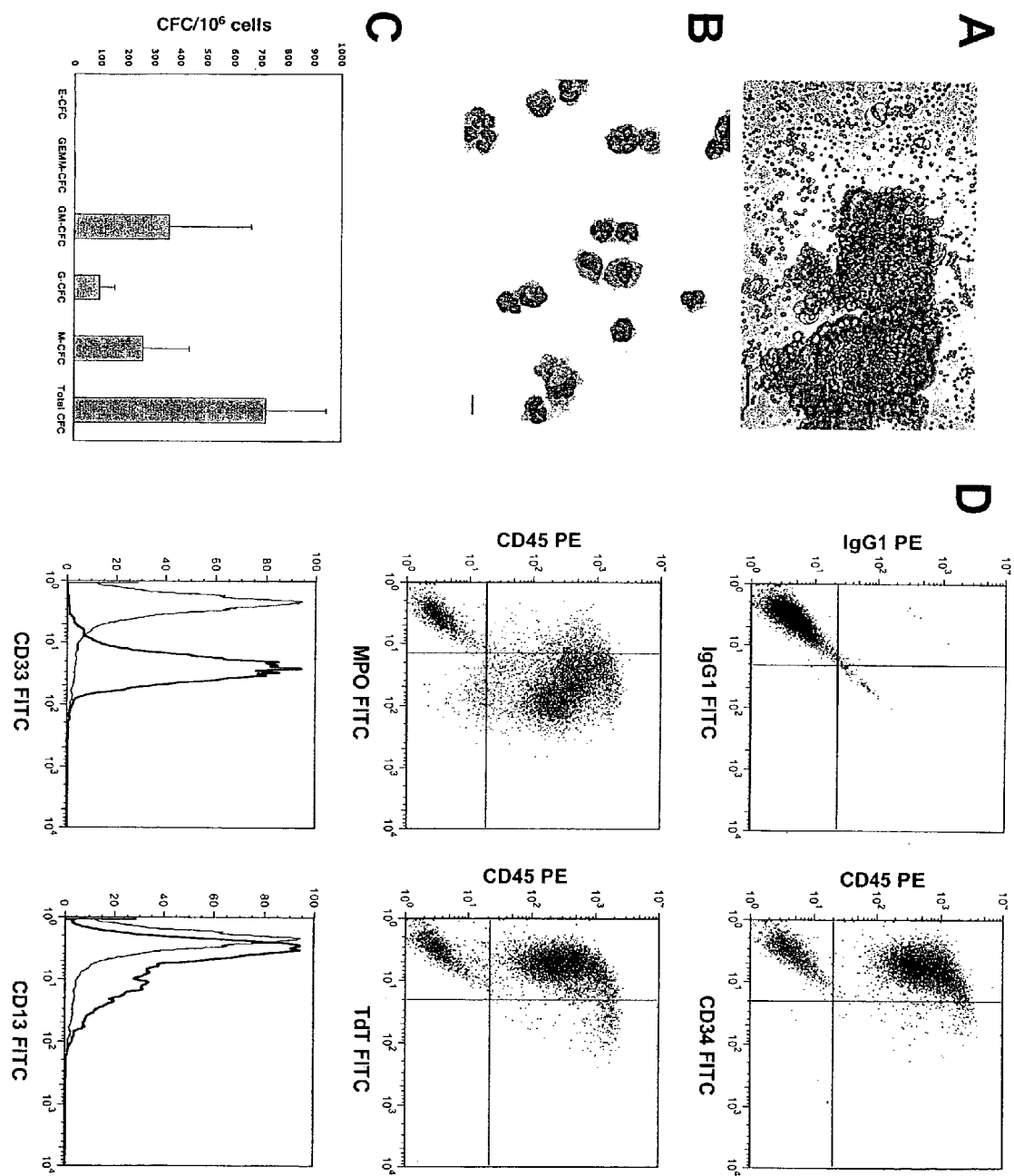
FIG. 2 illustrates the morphology and phenotypical features of myeloid precursor cells generated in step 2 of FIG. 1.

Recently we developed an in vitro culture system for hematopoietic differentiation from human ES cells, using cells of mouse M-CSF deficient bone marrow stromal cell line OP9 as feeder cells, a step used to start the protocols described here. Human ES cells were co-cultured with OP9 cells so that they would differentiate into CD34+ cells which are highly enriched in colony-forming cells and contain erythroid, myeloid, as well as lymphoid, progenitors and include a population of CD34+CD43+Lin− multipotent hemotopoietic progenitors. This step does not require cytokine addition. The maximal expansion of myeloid colony-forming cells (CFCs) in the OP9 co-culture system was observed on days 9 to 10 of differentiation. To induce selective expansion of myeloid progenitors, we harvested the resulting cells from days 9 or 10 of human ES cell/OP9 co-culture and cultured the cells in non-adherent conditions in presence of GM-CSF. At the beginning of culture, aggregates of large cells were formed. Approximately 3 days after initiation of GM-CSF culture, individual cells appeared and rapidly expanded. After 9-10 days of culture with GM-CSF, and following the removal of clumps and dead cells by Percoll separation, we obtained a population of cells of which 90% of the cells were CD45 positive. More than 90% of these CD45+ cells contained intracellular MPO (myeloperoxidase, a marker of myeloid cells) but not TdT (terminal deoxynucleotidyl transferase, a marker of lymphoid cells) and expressed a marker of myeloid progenitors, CD33. In addition, these human ES cell-derived myeloid cells were CD4 positive, and weakly expressed IL-3 receptor α-chain CD123. More than 50% of these cells expressed CD16, CD15, CD11b and CD11c (Table 2). Morphologically, the GM-CSF-expanded cells had multi-lobed or round nuclei and a moderate amount grayish, occasionally vacuolated, cytoplasm without visible granules (FIG. 2B), resembling bone marrow myelomonocytic precursors. Some of the GM-CSF-expanded cells retained myeloid CFC potential, but no erythroid or multi-lineage CFC potential was detected (FIG. 2C). In addition, a relatively small population of cells at advanced stages of maturation that expressed a moderate level of CD14, low level of CD1a as well as the HLA-DR, and CD80 and CD86 co-stimulator molecules were present (Table 2).

Cutaneous lymphocyte-associated antigen (CLA) expression on peripheral blood CD34+ cells defines progenitors which further differentiate into Langerhan's cells, while CD34+CLA− cell give rise to interstitial DC-like cells. No significant CLA expression was detected in the total cell population obtained from OP9 co-cultures or isolated human ES cell-derived CD34+ cells. However, CLA expression was found on a small subset of myeloid progenitors generated with GM-CSF.

GM-CSF appeared to be the most important factor in expansion of myeloid precursors. Separately, the addition of SCF, FLT3L, or SCF with FLT3L to GM-CSF-supplemented cultures had little effect on total cell output and myeloid CFCs numbers during 10 days of culture (Table 1). These data demonstrate that culture of differentiated human ES cells generated in OP9 system with GM-CSF predominantly expand into a unique population of CD45+CD4+ CD123$^{low}$myeloid precursors which include subpopulation of cells expressing MPO, M-CSFR, CD11b, CD11c, CD15 and CD16.

Differentiation of Human ES-Cell Derived Myeloid Precursors into Dendritic Cells.

Figure 3:
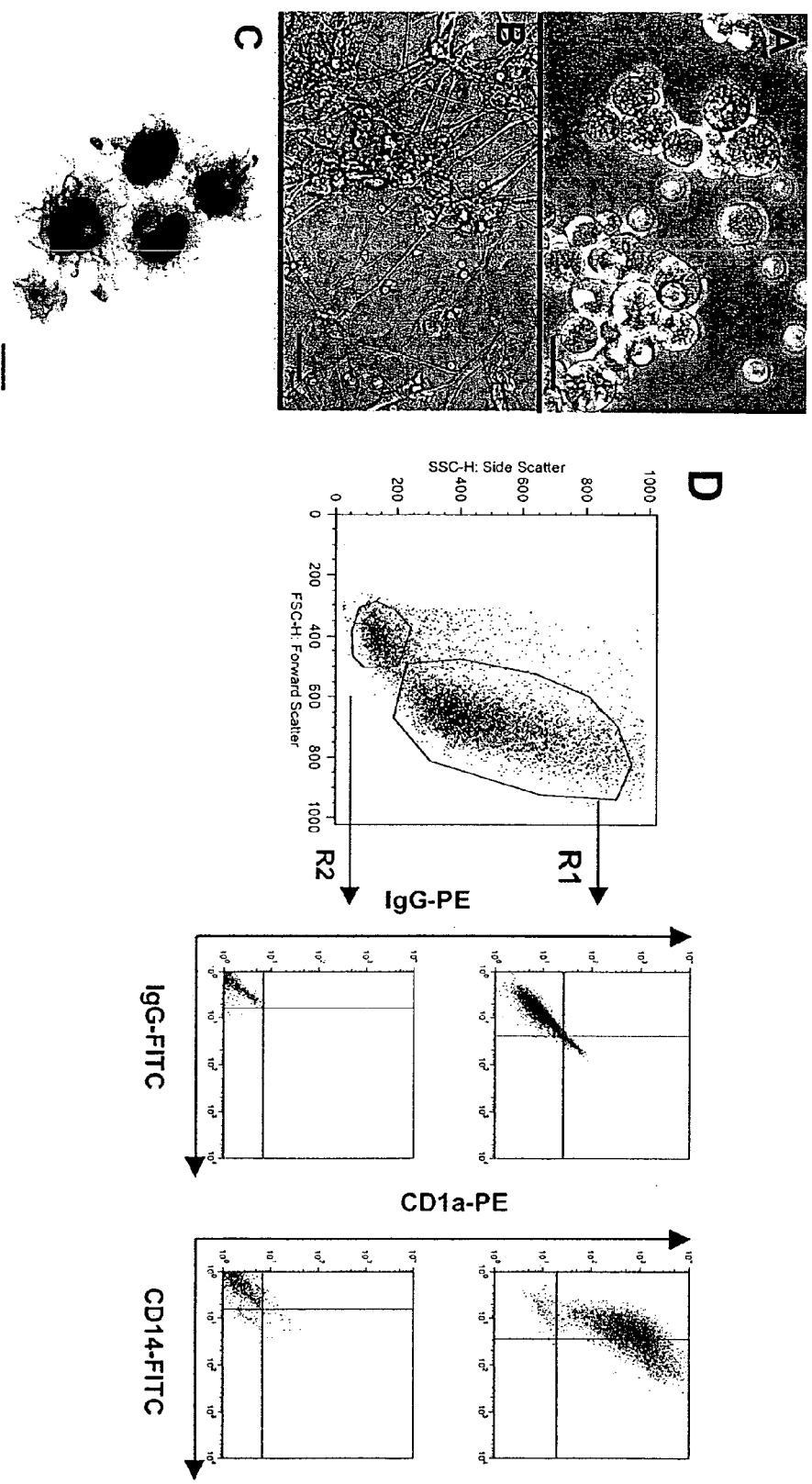
FIG. 3 illustrates the morphology and light scatter properties of hES cell-derived DSs. (A) Phase contrast micrograph of culture and (C) Wright-stained smears of differentiated H1 cells demonstrate numerous thin cytoplasmic processes ("veils"); (A) bar is 15 μm and (C) bar is 40 μm. (B) When cultured on flat-bottom ultralow attachment plates, cells form long dendrites; bar is 25 μm. (D) Light scatter properties and phenotype of cells obtained in step 3 after 9-day culture of hES cell-derived myeloid progenitors with GM-CSF and IL-4. Phenotypic analysis from representative experiments using the H1 cell line shows that R1-gated cells with a high scatter profile express CD1a and weakly CD14.

To induce differentiation of myeloid precursors into dendritic cells, we cultured the culture of precursor cells with GM-CSF and various combinations of IL-4, TNF-α, and IFN-α. In typical experiment, after 7-10 days of culture with GM-CSF and IL-4, most of the cells appeared as clumps. In addition, individual floating cells with well-defined dendrites appeared in the cultures. Morphologically, these cells were large, had high nuclear cytoplasmic ratio, and had oval or kidney-shaped nuclei and nonvacuolated, occasionally granular cytoplasm with very fine cytoplasmic processes (FIG. 3A and C). Based on flow cytometric analysis of size and granularity, two cell populations were observed (FIG. 3D): R1, cells with high scatter profile and dendritic cell phenotype; and R2, cells with a low scatter profile, which lacked dendritic cell markers and which were more phenotypically similar to myeloid progenitors generated in the second step. Dendritic cells identified as R1 gated cells expressed CD1a, DC-SIGN, CD4, CD11c, HLA-ABC and HLA-DR, CD80, and CD86. Additionally, these cells expressed a low level of CD9, CD11b, CD123, and CD40. CD14 expression was very weak, but detectable, and most of the CD14-positive cells co-expressed CD1a. However all cells were lacking CD83 expression.

In addition to IL-4, differentiation of myeloid precursors into dendritic cells was achieved by using other cytokines such as TNF-α and IFN-α or their combinations. However, most of the cells in cultures with TNF-α co-expressed low level of CD1a, high levels of CD14 and were lacking expression of CD9. In addition, in cultures with TNF-α, cells down-regulated expression of costimulatory molecules. As expected, addition of IFN-α to these cell cultures resulted in increased expression of MHC class I molecules. However, IFN-α culture resulted in a decreased number of CD1a+ cells, as well decreased CD14 expression. Similar to the monocyte-DC differentiation pathway, expression of DC-SIGN on human ES cell-derived dendritic cells was primarily dependent on IL-4. Based on cell yield, phenotypic, and functional properties (Table 1 and 2), we concluded that a combination of GM-CSF and IL-4 provides the best conditions for generation of functional dendritic cells from human ES cells.

By immunocytochemistry, human ES cell-derived dendritic cells were positive for CD68, but not strongly so, and expressed a very low level of intracytoplasmic but not membranous CD83. Fascin, an actin-binding protein that has been shown to be a highly selective marker of mature dendritic cells, was not detected. From this, we concluded that the dendritic cells generated by the process described so far were immature. To investigate whether these immature dendritic cells could be further matured, we treated cells generated from the above protocols with calcium ionophore A23187. This treatment resulted in the up-regulation of CD83, CD86 and HLA-DR expression. The intensity of intracytoplasmic CD68 staining substantially increased and perinuclear condensation of CD68 was evident in the cells so produced. In addition, some cells became fascin-positive. LPS, TNF-α, IL-1β, PGE2, and IL-6 were not efficient in induction of maturation of hES cell-derived DCs. Taken together, these data demonstrate that cells with typical dendritic cell morphology and phenotype can be generated from human ES cells.

The Dendritic Cells Induce Allogeneic T Cell Response and are Capable of Antigen Processing and Presentation.

We next investigated to determine whether our human ES cell-derived dendritic cells were fully functional as dendritic cells. As determined by DQ ovalbumin assay, human ES cell-derived dendritic cells were capable of taking up and processing antigen. Cells obtained in cultures treated with GM-CSF and IL-4 were the most efficient in antigen processing, while the dendritic cells differentiated with GM-CSF and TNF-α were less efficient.

A hallmark of the functionality of dendritic cells is their ability to stimulate naïve cells. By our tests, human ES cell-derived dendritic cells were able to trigger cord blood T cells, which are entirely naïve. Immature dendritic cells, generated in cultures with GM-CSF and IL-4 added, were the most powerful stimulatory cells, while addition of TNF-α to the cell culture significantly diminished ability of the cells to stimulate naïve T lymphocytes. In addition, the dendritic cells were able to stimulate adult donor T-cells.

To evaluate the capacity of dendritic cells to present antigens through the MHC class I pathway, we pulsed HLA-A02 H1 cell line-derived dendritic cells with inactivated CMV virus and evaluated the ability of the cells to stimulate HLA-A0201 restricted CMV-specific T cell clone HLA with specificity to CMV pp65 NLVPMVATV peptide. While the addition of dendritic cells to T-cells induced allogeneic response, a significant increase in response by the T cells was obtained when cells were stimulated with CMV pulsed H1-derived dendritic cells (Table 3). Altogether, these data demonstrate that our culture system allows generation of cells with phenotype, morphology and unique antigen-presenting properties characteristic of dendritic cells.

Methods and Materials

Cell Lines, Cytokines and Monoclonal Antibodies (mAbs).

Human ES cell lines H1 (passages 32-51) and H9 (passages 40-44) were maintained in an undifferentiated state by weekly passage on mouse embryonic fibroblasts. A mouse bone marrow stromal cell line OP9 was obtained from Dr. Toru Nakano (Research Institute for Microbial Diseases, Osaka University, Japan). This cell line was maintained on gelatinized 10 cm dishes (BD Bioscience, Bedford, MA) in OP9growth medium consisting of a-MEM (Invitrogen, Carlsbad, CA), supplemented with 20% defined fetal bovine serum (FBS; HyClone Laboratories, Logan, UT). Sterile, recombinant, endotoxin and pyrogen-free SCF, FLT3-L, TNF-α, IL-4 were obtained from Peprotech (Rocky Hill, N.J.), GM-CSF from Berlex Laboratories (Richmond, Calif.) and IFN-α from Schering Corporation (Kenilworth, N.J.). The following mouse anti-human mAbs without detectable cross-reactivity with murine cells have been used for flow cytometric analysis: CD1a-PE, CD4-PE, CD11b-FITC, CD16-PE, CD33-FITC, CD80-PE, CD86-PE, HLA-DR-PE, myeloperoxidase (MPO)-FITC, terminal deoxinucleotidyl transferase (TdT)-FITC (Caltag, Burlingame, CA); CD9-PE, CD14-FITC, CD40-PE, CD43-FITC, CD45-PE, CD209(DC-SIGN)-FITC, CLA-FITC (BD Pharmingen); CD11c-PE, CD34-PerCP-Cy5.5 (Becton Dickinson Immunocytometry Systems, San Jose, Calif.); CD83-FITC, CD208(DC-LAMP; Beckman Coulter, Miami, Fla); CD123-FITC (Miltenyi Biotech, Auburn, Calif.); HLA-ABC-FITC (Sigma, St.Louis, Mo.); CD207(Vector Laboratories).

Hematopoietic Differentiation of Human ES Cells in Co-Culture with OP9 Cells.

The induction of human ES cells differentiation into hematopoietic cells was done as previously described, Vodyanik, et al. 2005. *Blood* 105:617, which is incorporated herein by reference. Briefly, undifferentiated human ES cells were harvested by treatment with 1 mg/ml collagenase IV (Invitrogen) and added to OP9 cultures at approximate density of $1.5 \times 10^6/20$ ml per 10 cm dish in αMEM supplemented with 10% FBS (HyClone) and 100 μM Methyl β-D-thiogalactopyranoside (MTG)(Sigma, St.Louis, Mo.). Human ES cell/OP9 co-cultures were incubated for 9-10 days with a half medium change on days 4, 6, and 8 without added cytokines. The human ES cells then differentiated into hematopoietic cells.

Generation of Human ES Cell-Derived Dendritic Cells.

A schematic diagram of the protocol used for generation of dendritic cells from human ES cells is depicted in FIG. 1. On day 9-10 of human ES cell/OP9 co-culture, differentiated derivatives of human ES cells were harvested by treatment with collagenase IV (Invitrogen; 1 mg/ml in α-MEM) for 20 min at 37° C., followed by treatment with 0.05% Trypsin-0.5 mM EDTA (Invitrogen) for 15 min at 37° C. After trypsin inactivation by FBS, these cells were re-suspended in α-MEM supplemented with 10% FBS (HyClone) and 100 ng/ml GM-CSF, and transferred into tissue culture flasks (BD Bioscience) coated with poly 2-hydroxyethyl methacrylate (HEMA, Sigma) to prevent cell adherence. The cells were then cultured for 8-10 days with a half medium change every fourth day to expand dendritic cell precursors. To evaluate the effect of SCF and FLT3-L on the expansion of these human ES cell-derived dendritic cell precursors, we cultured the cells in the presence of (1) 100 ng/ml GM-CSF +20 ng/ml SCF; (2) 100ng/ml GM-CSF +50 ng/ml FLT3-L; or (3) 100 ng/ml GM-CSF +20 ng/ml SCF +50 ng/ml FLT3-L. Subsequently, the cells were spun over 20% Percoll (Sigma) to remove dead cells and cell aggregates. As a third step, Percoll-isolated cells were cultured for 7-9 days in HEMA-coated flasks in StemSpan® serum-free expansion medium (SFEM; Stem Cell Technologies, Vancouver, Canada) supplemented with lipid mixture 1 (Sigma) and 100 ng/ml GM-CSF, with the addition of the following cytokines: (1) 100 ng/ml IL-4, (2) 20 ng/ml TNF-α. (3) $10^4$U/ml IFN-α. and (4) 100 ng/ml IL-4+20 ng/ml TNF-α Cells were cultured for 7-9 days with a half medium change every fourth day. To further maturate dendritic cells, we cultured the cells obtained in step 3 in SFEM medium with 400 ng/ml of A23187 calcium ionophore (Sigma) for 48 hours.

Flow Cytometry Analysis

Cells were prepared in PBS-FBS (PBS containing 0.05% sodium azide, 1 mM EDTA, and 2% FBS), supplemented with 2% normal mouse serum (Sigma), and labeled with a combination of mAbs. Samples were analyzed using a FACSCalibur flow cytometer (BDIS) with CellQuest acquisition software (BDIS). List mode files were analyzed by FlowJo software (Tree Star, Inc., Ashland, Oreg.). Control staining with appropriate isotype-matched control mAbs (BD Pharmingen) was included to establish thresholds for positive staining and background linear scaled mean fluorescence intensity (MFI) values. The percentage (%) of positive cells was calculated as % of positive cells stained with specific mAb—% of background staining with corresponding isotype control. ΔMFI was calculated as MFI of cells stained with specific mAb-MFI of cells stained with corresponding isotype control. Linear scaled MFI was used as an indicator of relative antigen density on given cells.

Antigen Processing Assay

Ovalbumin (OA) processing assays were performed using self-quenched conjugate of ovalbumin (DQ-OVA; Molecular Probes, Eugene, Oreg.) that exhibits bright green fluorescence upon proteolytic degradation. Dendritic cells obtained as in step 3 of FIG. 1 were incubated with 100 μg/ml DQ-OVA for 30 min at 37° C. in DMEM/F12 (Invitrogen) containing 2% FBS, and 1% of non-essential amino acids. Cells incubated at 4° C. were used as a control for background fluorescence. OVA proteolysis was evaluated by flow cytometry.

Clonogenic Progenitor Cell Assay

Hematopoietic clonogenic assays were performed in 35 mm low adherent plastic dishes (Stem Cell Technologies) using a 1 ml/dish of MethoCult GF with H4435 semisolid medium (Stem Cell Technologies) consisting of 1% methylcellulose, 30% FBS, 1% BSA, 50 ng/ml SCF, 20 ng/ml granulocyte-macrophage colony stimulating factor (GM-CSF), 20 ng/ml IL-3, 20 ng/ml IL-6, 20 ng/ml granulocyte colony stimulating factor (G-CSF), and 3 units/ml erythropoietin. All clonogenic progenitor assays were performed in duplicates and CFCs were scored after 14-21 days of incubation according to their colony morphology as erythroid (E-CFC), granulocyte, macrophage, megakaryocyte (GEMM-CFC), granulocyte-macrophage (GM-CFC), granulocyte (G-CFC) and macrophage (M-CFC). The frequency of CFC was calculated per $10^6$ total cells.

Allogenic Mixed Lymphocyte Reaction (MLR)

Adult mononuclear cells were isolated from peripheral blood samples obtained from healthy laboratory volunteers by density gradient centrifugation on Histopaque-1077. Mononuclear cord blood cells were also purchased from Cambrex Bio Science (Walkersville, Md.). The mononuclear cells were depleted of monocytes by plastic adherence and used as responder cells. Graded numbers ($1 \times 10^3$ to $3 \times 10^4$/well) of irradiated (35Gy) stimulatory cells were co-cultured with $1 \times 10^5$ responder cells for 6 days in 96-well flat bottom plates (Corning) in RPPMI 1640 containing 5% human AB serum (Sigma). [3H]thymidine (Sigma) was added (1 μCi/well) during the last 16 hours of incubation. Cells were harvested onto glass fiber filters and incorporation of [3H]thymidine was measured by scintillation counting.

Although the foregoing invention has been described in some detail by way of illustration and example for purposes of clarity of understanding, it is understood that certain adaptations of the invention are a matter of routine optimization for those skilled in the art, and can be implemented without departing from the spirit of the invention, or the scope of the appended claims.

TABLE 1

Relative cell yield after each culture step*

| | Relative Cell Yield |
|---|---|
| Step 1 | 8.8 ± 4.4 |
| Step 2 | |
| GM-SCF | 5.5 ± 3.7 |
| GM-CSF + SCF | 5.6 ± 5.7 |
| GM-CSF + FLT3-L | 4.6 ± 4.2 |
| GM-CSF + SCF + FLT3-L | 5.1 ± 5.0 |
| Step 3 | |
| GM-CSF + IL-4 | 3.3 ± 4.1 |
| GM-CSF + TNF-α | 2.3 ± 1.7 |
| GM-CSF + IFN-α | 2.3 ± 1.6 |
| GM-CSF + IL-4 + TNF-α | 1.9 ± 1.3 |

*Relative cell yield at each step calculated as a number of cells obtained from one initially plated undifferentiated human ES cell (total number human ES cells plated on OP9/total number of cells obtained after corresponding step); results calculated as mean ± SD of 4 to 10 experiments.

TABLE 2

Phenotypic analysis of DCs induced by different cytokine combinations*

| Cell subset | | Step 2 | Step 3 GM-SCF + IL-4 | Step 3 GM-SCF + TNF-α | Step 3 GM-SCF + IL-4 + TNF-α | Step 3 GM-SCF + IFN-α |
|---|---|---|---|---|---|---|
| R1 gated cells | % | NA | 58.8 ± 12.3 | 45.5 ± 12.1 | 46.7 ± 14.9 | 39.9 ± 7.5 |
| CD1a | % | 3.3 ± 2.1 | 82.9 ± 12.4 | 66.9 ± 24.0 | 78.2 ± 7.7 | 30.3 ± 27.1 |
| | ΔMFI | | 750.2 ± 700.7 | 74.8 ± 60.8 | 148.3 ± 161.9 | 77.1 ± 72.1 |
| CD14 | % | 12.6 ± 7.1 | 25.6 ± 7.5 | 71.1 ± 12.2 | 39.0 ± 19.3 | 19.8 ± 15.1 |
| | ΔMFI | 14.7 ± 4.2 | 27.6 ± 15.5 | 55.3 ± 38.1 | 31.5 ± 29.0 | 60.7 ± 50.8 |
| DC-SIGN | % | <1 | 87.6 ± 7.7 | <2 | 84.7 ± 4.2 | 17.3 ± 15.4 |
| | ΔMFI | | 460.3 ± 352.0 | | 213.8 ± 160.1 | 40.2 ± 39.1 |
| CD83 | % | <1 | <1 | <1 | <1 | <1 |
| CD11c | % | 60.0 ± 14.2 | 94.1 ± 5.3 | 98.0 ± 1.6 | 93.7 ± 3.3 | 91.0 ± 8.5 |
| | ΔMFI | 132.1 ± 59.9 | 282.3 ± 37.2 | 202.3 ± 19.8 | 237.6 ± 17.8 | 97.4 ± 41.8 |
| CD11b | % | 59.4 ± 13.1 | 67.4 ± 29.0 | 48.8 ± 24.9 | 56.0 ± 5.4 | 59.6 ± 8.4 |
| | ΔMFI | 69.3 ± 23.0 | 52.9 ± 33.6 | 24.6 ± 14.3 | 47.9 ± 32.5 | 40.1 ± 35.3 |
| CD123 | % | 35.5 ± 14.6 | 58.8 ± 12.3 | 63.5 ± 16.6 | 45.1 ± 7.9 | 29.4 ± 18.6 |
| | ΔMFI | 27.8 ± 15.2 | 35.9 ± 14.6 | 28.3 ± 12.6 | 33.9 ± 20.1 | 18.9 ± 15.3 |
| HLA-ABC | % | 79.6 ± 8.8 | 90.3 ± 8.4 | 91.8 ± 4.1 | 84.8 ± 9.3 | 99.2 ± 0.9 |
| | ΔMFI | 125.7 ± 61.6 | 92.4 ± 10.6 | 130.3 ± 62.1 | 111.2 ± 55.4 | 258.0 ± 47.9 |
| HLA-DR | % | 14.9 ± 12.0 | 90.1 ± 6.3 | 90.1 ± 4.1 | 82.1 ± 8.0 | 89.4 ± 7.7 |
| | ΔMFI | 189.5 ± 83.7 | 597.0 ± 204.3 | 267.3 ± 123.1 | 208.3 ± 82.9 | 509.8 ± 340.2 |
| CD86 | % | 35.1 ± 9.1 | 93.4 ± 3.5 | 85.4 ± 7.3 | 90.1 ± 2.9 | 82.4 ± 14.1 |
| | ΔMFI | 60.2 ± 24.3 | 1767.4 ± 1122.3 | 158.5 ± 94.6 | 439 ± 131.0 | 125.3 ± 107.2 |
| CD80 | % | 7.9 ± 7.8 | 81.2 ± 21.8 | 84.8 ± 10.7 | 81.8 ± 11.6 | 81.6 ± 19.3 |
| | ΔMFI | | 621.2 ± 492.9 | 128.9 ± 80.4 | 295.8 ± 353.7 | 61.0 ± 13.2 |

TABLE 2-continued

Phenotypic analysis of DCs induced by different cytokine combinations*

| Cell subset | | Step 2 | Step 3 GM-SCF + IL-4 | Step 3 GM-SCF + TNF-α | Step 3 GM-SCF + IL-4 + TNF-α | Step 3 GM-SCF + IFN-α |
|---|---|---|---|---|---|---|
| CD40 | % | 4.6 ± 4.4 | 46.4 ± 16.9 | 43.3 ± 23.7 | 57.0 ± 1.6 | 53.9 ± 26.8 |
|  | ΔMFI |  | 27.0 ± 11.4 | 16.6 ± 5.2 | 47.2 ± 32.5 | 21.0 ± 10.2 |

*Results are mean ± SD of 4 to 5 independent experiments; for step 3 cultures % and ΔMFI of R1 gated cells calculated.

TABLE 3

Antigen-presenting capacity of H1-derived DCs*

| T Cells | DC | CMV | Proliferation (cpm) | IFN-γ (pg/ml) |
|---|---|---|---|---|
| + | − | − | 652 ± 129 | 0 |
| + | + | − | 17225 ± 579 | 224 ± 26.7 |
| + | + | + | 20303 ± 1279 | 326 ± 11.8 |

*HLA-A02 H1-derived dendritic cells (cells obtained in step 3 with GM-CSF + IL-4) incubated overnight with or without CMV virus and then added to the HLA-A0201 restricted allogeneic T cell clone with specificity to CMV pp65. Results expressed as a mean ± SD of triplicate.

We claim:

1. A method of culturing human embryonic stem cells into immature dendritic cells, the method comprising the steps of
    (a) co-culturing human embryonic stem cells with stromal cells that do not express macrophage colony-stimulating factor, wherein the stem cells are induced to differentiate into multipotent lympho-hematopoietic progenitor cells and wherein the culture is free of exogenously added cytokines;
    (b) culturing the progenitor cells with granulocyte/macrophage colony stimulating factor (GM-CSF) under non-adherent conditions to cause the expansion of myeloid precursors cells, wherein at least 90% of the cells obtained are CD45+, and at least 90% of the CD45+ cells also express MPO and CD33, but not TdT;
    (c) further differentiating the myeloid precursors in the presence of GM-CSF and IL-4 to form cells that have the phenotype of immature dendritic cells; and
    (d) recovering cells which have the phenotype of immature dendritic cells, wherein the immature dendritic cells are of myeloid lineage.

2. The method of claim 1 wherein the stromal cells are OP9 cells.

3. The method of claim 1 further including, between step (b) and step (c), the step of separating clumps of cells and dead cells from the cell culture.

4. A method of culturing human embryonic stem cells into immature dendritic cells, the method comprising the steps of
    (a) co-culturing human embryonic stem cells with stromal cells that do not express macrophage colony-stimulating factor, wherein the stem cells are induced to differentiate into multipotent lympho-hematopoietic progenitor cells and wherein the culture is free of exogenously added cytokines;
    (b) culturing the progenitor cells with granulocyte/macrophage colony stimulating factor (GM-CSF) under non-adherent conditions to cause the expansion of myeloid precursors cells; and
    (c) culturing the myeloid precursor cells with GM-CSF and TNFα or GM-CSF and IFN-α and recovering regulatory accessory cells, wherein the regulatory accessory cells are characterized by the markers CD1a$^{low}$, CD9−, CD80$^{low}$ and CD86$^{low}$.

* * * * *

UNITED STATES PATENT AND TRADEMARK OFFICE
CERTIFICATE OF CORRECTION

PATENT NO. : 7,811,821 B2
APPLICATION NO. : 11/443608
DATED : October 12, 2010
INVENTOR(S) : Igor I. Slukvin et al.

It is certified that error appears in the above-identified patent and that said Letters Patent is hereby corrected as shown below:

Column 6, line 57 "CD45+CD4+CD123$^{low}$ low myeloid" should be -- CD45+CD4+CD123$^{low}$ myeloid --

Signed and Sealed this
Twenty-second Day of February, 2011

David J. Kappos
*Director of the United States Patent and Trademark Office*